United States Patent [19]
Ishizuka et al.

[11] Patent Number: 5,952,380
[45] Date of Patent: Sep. 14, 1999

[54] METHOD FOR TREATING DIARRHEA

[75] Inventors: Masaaki Ishizuka, Mishima; Kenji Maeda, Meguro-ku; Tomio Takeuchi, Shinagawa-ku; Toshiyuki Toko, Itano-gun; Tadayoshi Shiraishi, Takasago, all of Japan

[73] Assignees: Zaidan Hojin Biseibutsu Kagaku Kenkyu Kai; Taino Pharmaceutical Co., Ltd., both of Tokyo; Kanegafuchi Kagaku Kogyo Kabushiki Kaisha, Osaka, all of Japan

[21] Appl. No.: 08/825,095

[22] PCT Filed: Oct. 13, 1995

[86] PCT No.: PCT/JP95/02107

§ 371 Date: Mar. 27, 1997

§ 102(e) Date: Mar. 27, 1997

[87] PCT Pub. No.: WO96/11681

PCT Pub. Date: Apr. 25, 1996

[30] Foreign Application Priority Data

Oct. 14, 1994 [JP] Japan ................... 6-249466
Aug. 15, 1995 [JP] Japan ................... 7-208201

[51] Int. Cl.$^6$ ............... A61K 31/195; A61K 31/16; A61K 31/045

[52] U.S. Cl. ............ 514/563; 514/557; 514/629; 514/669; 514/738; 514/867

[58] Field of Search ............... 514/23, 563, 867, 514/738, 557, 629, 669; 562/567; 568/852

[56] References Cited

U.S. PATENT DOCUMENTS

| | | | |
|---|---|---|---|
| 5,098,935 | 3/1992 | Ishizuka et al. | 514/563 |
| 5,447,719 | 9/1995 | Kamataki | 424/195.1 |

FOREIGN PATENT DOCUMENTS

| | | | |
|---|---|---|---|
| 4-112865 | 4/1992 | Japan | C07C 323/40 |
| 5-43469 | 2/1993 | Japan | A61K 31/70 |
| 6-65072 | 3/1994 | Japan | A61K 31/195 |
| WO 96/11681 | 4/1996 | WIPO . | |

*Primary Examiner*—Howard C. Lee
*Attorney, Agent, or Firm*—Sughrue, Mion, Zinn, Macpeak & Seas, PLLC

[57] ABSTRACT

A pharmaceutical composition for treating diarrhea comprising an anti-diarrhea effective amount of conagenin or a salt thereof, and a pharmaceutically acceptable carrier. The pharmaceutical composition is particularly useful against diarrhea caused by the administration of cancer chemotherapeutic agents.

6 Claims, No Drawings

METHOD FOR TREATING DIARRHEA

This Application is a National Stage under 35 U.S.C. § 371 of PCT International Application No. PCT/JP95/02107, filed Oct. 13, 1995.

TECHNICAL FIELD

The present invention relates to an agent for preventing and treating diarrhea, and particularly to a pharmaceutical agent for preventing and treating a diarrheic symptom caused by administration of cancer chemotherapeutics.

BACKGROUND ART

Diarrhea often develops as a side-effect disorder during the clinical treatment course by pharmacotherapy, whose typical symptom is characterized by the frequent defecation of liquid or liquid-like stools. In particular, the diarrhea due to the administration of cancer chemotherapeutics is often so serious that most patients with such a diarrhea symptom are no longer allowed to receive the further continuous treatment. Furthermore, this diarrhea endangers the patient's physical strength and nourishment, leading to slowing down the recovery pace from leukopenia, thrombocytopenia and the like, symptoms caused by administration of cancer chemotherapeutics.

There are already various chemotherapeutics widely used, for example, antimetabolites, such as 5-fluorouracil and derivatives thereof such as 5-fluorouracil, doxifluridine and tegafur, 5-fluorouridine, and methotrexate, compounds derived from plants, such as camptothecin, etoposide and vincristin sulfate, alkylating agents such as cyclophosphamide, anticancer antibiotics such as adriamycin and mitomycin C, cisplatin, and carboplatin, but these chemotherapeutics are known to commonly cause the foregoing diarrhea when used. In particular, this side effect is serious in the cases that its onset has been caused by, in particular, the continuous intravenous drip infusion of 5-fluorouracil or the administration of 5-fluorodeoxyuridine, doxifluridine, tegafur, cyclophosphamide, vincristine sulfate or irinotecan. So far, little is known about the detailed mechanism of diarrhea development. However, as far as cancer chemotherapeutics are concerned, it is speculated that diarrhea might be influenced pathologically by factors such as a direct affection to digestive tract mucosa, namely, chemical changes of mucosal cells, and further changes of enterobacterial flora. Yet there has been no established effective means for improving diarrheric symptom due to cancer chemotherapy, though effort is continued by some attempts such as alleviation of the diarrhea by changes in the usage and dose of cancer chemotherapeutics, improvement in their preparations, modification and conversion of compounds.

However, none of such attempts have seen sufficient improvement against the foregoing diarrhea symptoms as yet. Thus, there is growing demand for development of an agent for preventing and treating diarrhea, which has higher safety and stronger efficacy.

As described above, the present state is such that there are not yet any efficacious and safe agents for preventing and treating diarrhea, specifically a pharmaceutical agent for alleviating diarrhea due to cancer chemotherapy. It is therefore an object of the present invention to provide an excellent agent for preventing and treating diarrhea.

The present inventors have thus carried out an extensive investigation. As a result, it has been found that conagenin or a salt thereof is efficacious against various diarrheic symptoms, in particular, a diarrheic symptom due to cancer chemotherapy, thus leading to completion of the present invention.

DISCLOSURE OF THE INVENTION

Namely, the present invention is directed to an agent for preventing and treating diarrhea, comprising conagenin or a salt thereof as an active ingredient.

The present invention is also directed to use of conagenin or a salt thereof for the preparation of an agent for preventing and treating diarrhea.

The present invention is further directed to a method of preventing and treating diarrhea, which comprises administering an effective amount of conagenin or a salt thereof to a patient with diarrhea.

BEST MODE FOR CARRYING OUT THE INVENTION

Conagenin is a compound represented by the following structural formula, and termed "(2 S)N-[(2 R,3 S,4 R)2,4-dihydroxy-3-methyl-pentanoyl]-2-methylserine" in nomenclature.

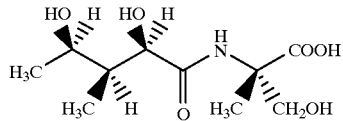

Conagenin has been already known as a chemotherapeutical agent for cancers (Japanese Patent Application Laid-Open No. 306953/1990 or U.S. Pat. No. 5,098,935), and also to be very low toxic agent. Among other acknowledged features of conagenin are the ability of enhancing proliferation of thrombocytes and leukocytes (Japanese Patent Application Laid-Open No. 229939/1993), and the capability of protecting a patient's body from the systemic lethal side effect during the clinical treatment for cancer, which is performed by use of anticancer agents such as adriamycin and cyclophosphamide, or during the radiotherapy, thereby making it possible to prolong the patient's life (Japanese Patent Application Laid-Open No. 65072/1994). However, nothing has been known about the effect of conagenin on diarrhea.

In accordance with the present invention, no particular limitation is imposed on the salt of conagenin so far as it is a pharmaceutically acceptable salt. Examples thereof include metal salts of the carboxyl group in conagenin, particularly, salts with alkali metals such as sodium and potassium and salts with alkaline earth metals such as calcium and magnesium, and an ammonium salt.

Conagenin can be collected from cultures of a conagenin-producing strain belonging to the genus Streptomyces, and can be obtained in accordance with, for example, the preparation process described in Japanese Patent Application Laid-Open No. 306953/1990.

Conagenin has low toxicity. For example, in an acute toxicity test on rats, the $LD_{50}$ value of conagenin was observed at a level of 500 mg/kg or more irrespective of variant routes such as oral administration, subcutaneous administration, intraperitoneal administration and intravenous administration.

The agent for preventing and treating diarrhea according to the present invention is particularly useful in preventing and treating the diarrhea occurring due to administration of cancer chemotherapeutics, not including conagenin or salts thereof.

Representative chemotherapeutics, which are responsible for diarrhea development but can be improved by the agent for preventing and treating diarrhea according to the present invention, include various anticancer agents, for example, antimetabolites, such as 5-fluorouracil and derivatives thereof such as 5-fluorouracil, doxifluridine, tegafur, carmofur and 3-[-3-(6-benzoyloxy-3-cyano-2-pyridyloxycarbonyl)benzoyl]-1-ethoxymethyl-5-fluorouracil, 5-fluorouridine, and methotrexate, compounds derived from plants, such as camptothecin, etoposide, vindesine sulfate and vincristin sulfate, alkylating agents such as cyclophosphamide and ranimustine, anticancer antibiotics such as adriamycin, pirarubicin and mitomycin C, and platinum compounds such as cisplatin and carboplatin. Preferable examples thereof include the antimetabolites such as 5-fluorouracil, derivatives thereof and 5-fluorouridine, the alkylating agents such as cyclophosphamide, and the compounds derived from plants, such as camptothecin and vincristin sulfate, with 5-fluorouracil, derivatives thereof, cyclophosphamide and vincristin sulfate being particularly preferred.

The agent for preventing and treating diarrhea according to the present invention can be prepared in various dose forms while formulated singly by conagenin or a salt thereof, and administered with separately prepared chemotherapeutics also having various dose forms. However, it is also possible to mix both agents with each other in advance, and then make the mixture various administration forms, and thereafter administer it.

The agent for preventing and treating diarrhea according to the present invention can be prepared as medicinal compositions by blending conagenin or a pharmaceutically acceptable salt thereof with carriers for preparations generally used. As the carriers, there may be used various kinds of carriers commonly used in usual drugs, for example, excipients, binders, disintegrators, lubricants, colorants, taste corrigents, smell corrigents, surfactants, etc.

The agent for preventing and treating diarrhea according to the present invention can be prepared in any administration form of oral preparations, injections, rectal suppositories and external preparations. In accordance with the present invention, an injection form can be prepared through the production process in which a pH adjuster, a buffer, a stabilizer and the like are added to an aqueous solution of conagenin or a salt thereof as an active ingredient, and the mixture is lyophilized in accordance with a method known per se in the art, thereby preparing a lyophilized injection preparation. It is also possible to obtain any one of subcutaneous, intramuscular and intravenous injection forms through the modified preparation process in which sterile water, a pH adjuster, a buffer, an isotonicity-imparting agent, a local anesthetic and the like are added to conagenin in accordance with a method known per se in the art.

In accordance with the present invention, an oral solid form can be prepared through the production process in which a solid carrier, and optionally a binder, a disintegrator, a lubricant, a colorant, a taste corrigent, a smell corrigent and/or the like may be added to conagenin or a salt thereof, and the mixture may then be formed into tablets, coated tablets, granules, powder, capsules, pills or the like in accordance with a method known per se in the art. Examples of the solid carrier used herein include starch, crystalline cellulose, gelatin, lactose, starch, magnesium stearate and the like. In preparation of this solid form, conagenin or a salt thereof may be incorporated in a proportion of 0.2–90% (by weight).

In accordance with the present invention, an oral liquid preparation can be prepared through the production process in which a taste corrigent, a buffer, a stabilizer, a smell corrigent and the like may be added to conagenin or a salt thereof to form the mixture into a solution, suspension, emulsion, syrup, dry syrup or elixir in accordance with a method known per se in the art.

In accordance with the present invention, a rectal suppository form can be prepared through the production process in which an excipient, and optionally a surfactant and an absorbefacient may be added to conagenin or a salt thereof, and the mixture may then be formed into a suppository in accordance with a method known per se in the art In accordance with the present invention, ointment forms, such as paste, cream and gel, can be prepared through the production process in which a base, a stabilizer, a wetting agent, a preservative and the like, which are routinely used, are incorporated into conagenin or a salt thereof as needed, and the components are mixed to formulate the desired preparations in accordance with a method known per se in the art. Examples of the base include liquid paraffin, white petrolatum, bleached bees wax, octyldodecyl alcohol and paraffin. Examples of the preservative include methyl p-hydroxybenzoate, ethyl p-hydroxybenzoate and propyl p-hydroxybenzoate.

In accordance with the present invention, a plaster form can be prepared by applying an ointment, cream, gel, paste or the like, in which conagenin or a salt thereof has been incorporated, to a support routinely used in a method known per se in the art. As the support, a fabric or nonwoven fabric made of cotton, rayon or chemical fibers, or a film or foamed sheet of soft polyvinyl chloride, polyethylene or polyurethane is suitable.

There is no particular limitation to administration routes in the present invention, that is, administration routes such as enteral administration, oral administration, rectal administration, intraoral administration and percutaneous administration are optionally depending on a preparation form, the age, sex and other conditions of a patient to be dosed, the diseased condition of the patient, and the like. For example, the tablets, granules, capsules, pills, solution, suspension and emulsion are orally administered, and on the other hand the suppository is intrarectally administered. The injection is intravenously administered singly or in combination with a usual supplemental solution containing glucose, amino acids and/or the like, and if needed, this administration is intraarterially, intramuscularly, intracutaneously, subcutaneously or intraperitoneally available with no combination use. The ointments are applied to the skin, oral mucosa membrane, etc.

The dose of the agent for preventing and treating diarrhea according to the present invention is determined depending on the age, weight, sex and diseased condition of a patient to be dosed, the object of therapy, and the like. However, it is normally preferred that the parenteral dose should be determined in the range of 0.1 mg to 500 mg per day in terms of conagenin content and the oral dose in the range of 0.5 mg to 2.5 g per day. Meanwhile, the administration may be divided into 2–4 times per day, or may be once per day.

EXAMPLES

The present invention will hereinafter be described in more detail by the following examples.

Test Example 1

Suppressing effect (1) on diarrhea caused by 5-fluorouracil:

To investigate the alleviating effect of conagenin on the diarrhea caused by the high level dosing of 5-fluorouracil, the following test was conducted.

Immediately before the administration of conagenin, 5-fluorouracil was intravenously administered to cynomolgus monkeys in a dose of 50 mg/kg (20-minute continuous drip infusion) at the starting day and the second day. Conagenin was intravenously administered to crab-eating macaques of two test groups (test groups: 3 monkeys per group) in doses of 1.25 and 5 mg/kg (dose volumes were both 0.5 ml/kg), respectively, which was carried out through veins of their limbs every day from the first day to the fourteenth day of the test. A control group (3 monkeys) was intravenously administered with 5-fluorouracil, and with Japanese pharmacopoeial physiological saline in place of conagenin. Thereafter, the defecated stools were visually examined and noted down for test analysis on the alleviating effect of conagenin on the diarrhea caused by high level dosing of 5-fluorouracil.

The following criteria were used as indices representing each form of the stools:

Normal stool: -

No evacuation: N

Loose stool: S

Watery diarrheic stool: W

Mucous stool: M

Bloody stool: B.

usually lead to death, conagenin was expected to exhibit a strong effect against an extremely detrimental diarrheic symptom, too.

Test Example 2

Suppressing effect (2) on diarrhea caused by 5-fluorouracil:

To investigate the alleviating effect of conagenin on the diarrhea caused by the continuous intravenous drip infusion of 5-fluorouracil (5-FU), the following test was conducted.

Tumorbearing animal models were prepared by subcutaneously implanting Yoshida sarcoma (number of cells: $2 \times 10^5$ cells) in male Donryu rats (aged 6 weeks) from their backs.

The thus-obtained models were subjected to continuous intravenous drip infusion of 5-fluorouracil in a dose of 40 mg/kg/day for 6 days from the first day of the test, and these models will be hereinafter referred to as a "group singly

TABLE 1

| | | | | | | | Conditions of stool | | | | | | | |
|---|---|---|---|---|---|---|---|---|---|---|---|---|---|---|
| Group | Animal No. | Before test | 1st day | 2nd day | 3rd day | 4th day | 5th day | 6th day | 7th day | 8th day | 9th day | 10th day | 11th day | 12th day | 13th day |
| Control group | 1 | — | — | — | — | S | —/S | S/W | S | S | —/S/W | | | | |
| | 2 | — | — | —/S | — | —/W | W | W | S | S | — | — | — | — | — |
| | 3 | — | — | — | — | — | —/W | W | —/S/W | —/S | —/S | — | — | — | — |
| Administration group of 1.25/kg of conagenin | 4 | — | — | — | — | — | — | S/W | S/W | S/W | S | S | S | —/S | — |
| | 5 | — | — | — | — | — | —/S | —/S | —/S | S | S/W | S | S | —/S | — |
| | 6 | —/S | — | — | — | — | —/W | S/W | —/S | S | S | — | — | — | — |
| Administration group of 5.0 mg/kg of conagenin | 7 | — | — | — | — | — | — | —/S | —/S | S | — | — | — | — | — |
| | 5 | — | — | — | — | — | — | — | — | —/S | — | — | — | — | — |
| | 9 | — | — | — | — | — | —/S/M/B | S/W | S | S | — | — | — | — | — |

In the control group to which the physiological saline was administered, diarrhea was observed on all the three monkeys for a period of days 4 to 9 counting from the starting day of 5-fluorouracil administration. On the other hand, in the group dosed with 1.25 mg/kg of conagenin, diarrhea was observed to significantly decrease as apparent from the results shown in Table 1. In the group dosed with 5 mg/kg of conagenin, diarrhea almost disappeared. It was hence confirmed that conagenin has a dosedependent suppressing effect on the diarrhea caused by 5-fluorouracil.

In the group dosed with 5 mg/kg of conagenin, a mixture of bloody and mucous stools, which is a symptom indicating a critical condition of diarrhea, as well as an apparent diarrheic symptom was observed at the fifth day and the sixth day, respectively. However, both symptoms disappeared within a few days thereafter. Taking into account the fact that most of cases accompanied by such symptoms dosed with 5-fluorouracil". With respect to a group (experiment group) administered with 5-fluorouracil plus conagenin, 20 mg/kg of conagenin were intravenously dosed to the tumorbearing rats beforehand treated with 5-fluorouracil every day from the first day to the seventh day of the test. On the seventh day of the test, both groups were inspected over the following observational points, i.e., changes in body weight, degrees of damage to digestive tracts (from autopsy findings) and changes in tumor weight, to investigate the alleviating effect of conagenin on the diarrhea caused by the continuous intravenous drip infusion of 5-fluorouracil and the influence of conagenin on the tumor-reducing effect of 5-fluorouracil.

The results are shown in Table 2.

TABLE 2

| | Dose of agent (mg/kg/day) | | Number of animals used | Tumor weight on 7th day (g ± SD) | Average body weight (g) | | Percent change in body weight against untreated group (%) | Degree and incidence of damage to digestive tract | | |
|---|---|---|---|---|---|---|---|---|---|---|
| | 5-FU | Conagenin | | | First day of test | Last day of test | | None | Slight | medium |
| Untreated group | 0 | 0 | 6 | 2.61 ± 0.60 | 222.1 | 239.3 | — | 6 | 0 | 0 |
| Group singly dosed with 5-FU | 40 | 0 | 7 | 0.04 ± 0.07 | 226.1 | 200.9 | −146.4 | 0 | 2 | 5 |
| Group dosed with 5-FU and conagenin | 40 | 20 | 8 | 0.01 ± 0.02 | 227.4 | 217.0 | −60.5 | 0 | 7 | 1 |

In the group administered with 5-fluorouracil plus conagenin, their digestive tracts were only slightly damaged compared with the group singly dosed with 5-fluorouracil, and their body weights were also well maintained compared with the control group. Thus, it was confirmed that conagenin works effectively for improving digestive tract damage caused by the continuous intravenous drip infusion of 5-fluorouracil and has a strong suppressing effect on the diarrhea.

Test Example 3
Suppressing effect on diarrhea caused by UFT:

To investigate the alleviating effect of conagenin on the diarrhea caused by the daily oral administration of UFT (trade mark, product of TAIHO PHARMACEUTICAL CO., LTD., a formulated preparation containing tegafur and uracil at a molar ratio of 1:4; hereinafter referred to as UFT merely), the following test was conducted.

Tumorbearing animal models were prepared by subcutaneously implanting Yoshida sarcoma (number of cells: $2 \times 10^4$ cells) in male Donryu rats (aged 5 weeks) from their backs.

The thus-obtained models were orally dosed with UFT in a dose of 40 mg/kg in terms of tegafur every day from the first day to the seventh day of the test, and these models will be hereinafter referred to as a "group singly dosed with UFT". With respect to a group (experiment group) administered with UFT plus conagenin, 20 mg/kg of conagenin were intravenously dosed to the tumorbearing rats beforehand treated with UFT every day from the first day to the seventh day of the test. On the seventh day of the test, both groups were inspected over the following observational points, i.e., changes in body weight, degrees of damage to digestive tracts (from autopsy findings) and changes in tumor weight, to investigate the alleviating effect of conagenin on the diarrhea caused by the continuous intravenous drip infusion of UFT.

The results are shown in Table 3.

In the group administered with UFT plus conagenin, their digestive tracts were only slightly damaged compared with the group singly dosed with UFT, and no damage to the digestive tract was observed on the models more than a half in particular. Besides, their body weights were also well maintained compared with the control group. Thus, it was confirmed that conagenin works effectively for improving the digestive tract damage by the sequential oral administration of UFT and has a strong suppressing effect on the diarrhea.

Test Example 4
Suppressing effect on diarrhea caused by doxifluridine:

To investigate the alleviating effect of conagenin on the diarrhea caused by the sequential oral administration of doxifluridine (hereinafter referred to as 5'-DFUR)), the following test was conducted.

Male $CDF_1$-mice (aged 7 weeks) were orally dosed with 5'-DFUR in a dose of 2 mmol/kg every day from the first day to the seventh day of the test, and these mice will be hereinafter referred to as a "group singly dosed with 5'-DFUR". With respect to a group (experiment group) administered with 5'-DFUR plus conagenin, 50 mg/kg of conagenin were intravenously dosed to the mice beforehand treated with 5'-DFUR every day from the first day to the tenth day of the test. On each day of ninth to thirteenth of the test, both groups were inspected over the following observational points, i.e., the conditions of stools and survival days to investigate the alleviating effect of conagenin on the diarrhea caused by the sequential oral administration of 5'-DFUR.

The results are shown in Table 4.

TABLE 3

| | Dose of agent (mg/kg/day) | | Number of animals used | Change in body weight (g) | Percent change in body weight against untreated group (%) | Degree and incidence of damage to digestive tract | | |
|---|---|---|---|---|---|---|---|---|
| | UFT*[1] | Conagenin | | | | None | Slight | medium |
| Untreated group | 0 | 0 | 13 | 44.2 | — | 13 | 0 | 0 |
| Group singly dosed with UFT | 40 | 0 | 7 | 4.6 | 3.0 | 0 | 5 | 2 |
| Group dosed with UFT and conagenin | 40 | 20 | 5 | 25.8 | 16.7 | 3 | 2 | 0 |

*[1]: The dose of UFT was expressed in terms of the amount of tegafur.

TABLE 4

| | Dose of agent | | | Incidence of normal/loose/diarrheic stools | | | | | |
|---|---|---|---|---|---|---|---|---|---|
| | 5'-DFUR (mmol/kg/ day) | Conagenin (mg/kg/ day) | Number of animals used | 9th day | 10th day | 11th day | 12th day | 13th day | Average survival days (days ± SD) |
| Untreated group | 0 | 0 | 5 | 5/0/0 | 5/0/0 | 5/0/0 | 5/0/0 | 5/0/0 | — |

TABLE 4-continued

| | Dose of agent | | | Incidence of normal/loose/diarrheic stools | | | | | |
|---|---|---|---|---|---|---|---|---|---|
| | 5'-DFUR (mmol/kg/ day) | Conagenin (mg/kg/ day) | Number of animals used | 9th day | 10th day | 11th day | 12th day | 13th day | Average survival days (days ± SD) |
| Group singly dosed with 5'-DFUR | 2 | 0 | 10 | 7/3/0 | 4/5/1 | 3/6/1 | 2/4/3 | 5/0/2 | 11.5 ± 1.3 |
| Group dosed with 5'-DFUR and conagenin | 2 | 50 | 10 | 9/1/0 | 8/2/0 | 8/2/0 | 9/1/0 | 10/0/0 | >14.0 |

In the group administered with 5'-DFUR plus conagenin, incidence of the watery diarrheic stools and loose stools were fewer compared with the group singly dosed with 5'-DFUR. Besides, the average survival days determined at the fourteenth day of the test also increased. Thus, it was confirmed that conagenin markedly suppresses the diarrhea caused by the daily oral administration of 5'-DFUR.

Test Example 5

Suppressing effect on diarrhea caused by cyclophosphamide:

To investigate the alleviating effect of conagenin on the diarrhea caused by the administration of cyclophosphamide, the following test was conducted.

Male Donryu rats (aged 5 weeks) were intraperitoneally dosed with cyclophosphamide in a dose of 90 mg/kg on the first day of the test and these rats will be hereinafter referred to as a "group singly dosed with cyclophosphamide". With respect to a group (experiment group) administered with cyclophosphamide plus conagenin, 50 mg/kg of conagenin were intravenously dosed to the rats beforehand treated with cyclophosphamide every day from the first day to the tenth day of the test. On the day (the fourth day) the diarrhea most occurred, both groups were compared with each other in the number of occurrences of diarrhea to investigate the alleviating effect of conagenin on the diarrhea caused by the administration of cyclophosphamide.

The results are shown in Table 5.

In the group administered with cyclophosphamide plus conagenin, incidence of the diarrhea was decreased to a half compared with the group singly dosed with cyclophosphamide. Thus, it was hence confirmed that conagenin has an improving effect on the diarrhea caused by the administration of cyclophosphamide.

Test Example 6

Suppressing effect on diarrhea caused by vincristine sulfate:

To investigate the alleviating effect of conagenin on the diarrhea caused by the administration of vincristine sulfate, the following test was conducted.

Male Donryu rats (aged 5 weeks) were intraperitoneally dosed with vincristine sulfate in a dose of 0.75 mg/kg on the first day of the test, and these rats will be hereinafter referred to as a "group singly dosed with vincristine sulfate". With respect to a group (experiment group) administered with vincristine sulfate plus conagenin, 50 mg/kg of conagenin were intravenously dosed to the rats beforehand treated with vincristine sulfate every day from the first day to the twelfth day of the test. From the second day to the twelfth day of the test, both groups were inspected over the following observational points, i.e., incidence of diarrhea and general symptoms to investigate the alleviating effect of conagenin on the diarrhea caused by the administration of vincristine sulfate.

The results are shown in Table 6.

TABLE 5

| | Dose of agent | | | |
|---|---|---|---|---|
| | Cyclophosphamide (mg/kg) | Conagenin (mg/kg/day) | Number of animals used | Incidence of diarrhea at the fourth day |
| Group singly dosed with cyclophosphamide | 90 | 0 | 10 | 10 |
| Group dosed with cyclophosphamide and conagenin | 90 | 50 | 10 | 5 |

TABLE 6

| | Dose of agent | | Number | Incidence of diarrhea | | | | | | | | | | |
|---|---|---|---|---|---|---|---|---|---|---|---|---|---|---|
| | Vincristine sulfate (mg/kg) | Conagenin (mg/kg/day) | of animals used | 2nd day | 3rd day | 4th day | 5th day | 6th day | 7th day | 8th day | 9th day | 10th day | 11th day | 12th day |
| Group singly dosed with vincristine sulfate | 0.75 | 0 | 10 | 10 | 10 | 10 | 10 | 10 | 6 | 10 | 10 | 10 | 10 | 7 |
| Group dosed with vincristine sulfate and conagenin | 0.75 | 50 | 10 | 8 | 7 | 7 | 7 | 7 | 7 | 7 | 7 | 7 | 4 | 2 |

In the group administered with vincristine sulfate plus conagenin, incidence of diarrhea was decreased compared with the group singly dosed with vincristine sulfate, and their recovery from diarrheric symptom was faster. Besides, the general symptoms during the period of observation and toxic symptoms recognized from the observation were also slight. Thus, it was confirmed that conagenin has an improving effect on the diarrhea caused by the administration of vincristine sulfate.

Preparation Example 1: Tablet preparation

| Conagenin | 60 mg |
|---|---|
| Starch | 112 mg |
| Magnesium stearate | 18 mg |
| Lactose | 45 mg |
| Total | 235 mg. |

A tablet preparation having the above formulation per tablet was produced in accordance with a method known per se in the art.

Preparation Example 2: Injection preparation

| Conagenin | 50 mg |
|---|---|
| Distilled water for injection | q.s. |
| One ampule contained | 5 ml. |

An injection preparation having the above formulation per ampule was produced in accordance with a method known per se in the art.

Preparation Example 3: Suppository preparation

| Conagenin | 100 mg |
|---|---|
| Witepsol W-35 (trade mark, product of Dynamite Nobel Co.) | 1400 mg |
| One suppository contained | 1500 mg. |

A suppository preparation having the above formulation per suppository was produced in accordance with a method known per se in the art.

Preparation Example 4: Injection preparation

| Conagenin | 10 mg |
|---|---|
| 5-Fluorouracil | 50 mg |
| Distilled water for injection | q.s. |
| One ampule contained | 5 ml. |

An injection preparation having the above formulation per ampule was produced in accordance with a method known per se in the art.

INDUSTRIAL APPLICABILITY

The agent for preventing and treating diarrhea according to the present invention has an excellent suppressing effect, in particular, which is very strong against the diarrheic symptom caused by administration of cancer chemotherapeutics. Therefore, not only does this agent make it possible to continue a prolonged cancer chemotherapy with no risk occurring by the diarrheic symptom inherent to the therapy, but also provides a strong effective means for cancer therapy without causing any patient's physical loss.

We claim:

1. A method for treating diarrhea comprising administering to a subject afflicted with diarrhea, an anti-diarrhea effective amount of conagenin or a salt thereof.

2. The method as claimed in claimed in claim 1, wherein said diarrhea is caused by the administration of a cancer chemotherapeutic agent.

3. The method as claimed in claim 2, wherein said cancer chemotherapeutic agent is an anti-metabolite, an alkylating agent or a compound derived from a plant.

4. The method as claimed in claim 3, wherein said cancer chemotherapeutic agent is an anti-metabolite or a compound derived from a plant.

5. The method as claimed in claim 2, wherein said cancer chemotherapeutic agent is 5-fluorouracil or a derivative thereof, cyclophosphamide, camptothecin or vincristine sulfate.

6. The method as claimed in claim 5, wherein said cancer chemotherapeutic agent is 5-fluorouracil or a derivative thereof, or vincristine sulfate.

* * * * *

UNITED STATES PATENT AND TRADEMARK OFFICE
CERTIFICATE OF CORRECTION

PATENT NO. : 5,952,380
DATED : September 14, 1999
INVENTOR(S) : Ishizuka, et al.

It is certified that error appears in the above-identified patent and that said Letters Patent is hereby corrected as shown below:

On the Cover Page, in the [73] Assignees: section of Column 1, change

"Zaidan Hojin Biseibutsu Kagaku Kenkyu Kai; <u>Taino</u> Pharmaceutical Co., Ltd., both of Tokyo; Kanegafuchi Kagaku Kogyo Kabushiki Kaisha, Osaka, all of Japan",
to
-- Zaidan Hojin Biseibutsu Kagaku Kenkyu Kai; Taiho Pharmaceutical Co., Ltd., both of Tokyo; Kanegafuchi Kagaku Kogyo Kabushiki Kaisha, Osaka, all of Japan --.

Signed and Sealed this

Fourteenth Day of March, 2000

Attest:

Q. TODD DICKINSON

*Attesting Officer*      *Commissioner of Patents and Trademarks*